United States Patent [19]
Shanbrom

[11] Patent Number: 5,589,072
[45] Date of Patent: Dec. 31, 1996

[54] TRACE CAPTURE IN BIOLOGICAL FLUIDS

[76] Inventor: Edward Shanbrom, 2252 Liane La., Santa Ana, Calif. 92705

[21] Appl. No.: 507,761

[22] Filed: Jul. 26, 1995

[51] Int. Cl.$^6$ .......................... B01D 15/00; A61M 1/14
[52] U.S. Cl. .................. 210/638; 210/651; 210/681; 210/683; 210/335; 422/44
[58] Field of Search .................. 422/44, 45, 28; 210/638, 651, 681, 683

[56] References Cited

U.S. PATENT DOCUMENTS

| | | |
|---|---|---|
| 4,017,407 | 4/1977 | Cantor et al. . |
| 4,022,882 | 5/1977 | Ely . |
| 4,098,728 | 7/1978 | Rosenblatt . |
| 4,247,393 | 1/1981 | Wallace .......................... 210/638 |
| 4,314,997 | 2/1982 | Shanbrom . |
| 4,612,122 | 9/1986 | Ambrus et al. .................. 210/638 |
| 4,789,545 | 12/1988 | Woods et al. . |
| 4,888,118 | 12/1989 | Barnes et al. . |
| 5,071,648 | 12/1991 | Rosenblatt . |
| 5,185,371 | 2/1993 | Rubinstein . |
| 5,211,912 | 5/1993 | Rubinstein . |
| 5,360,605 | 11/1994 | Shanbrom . |
| 5,370,869 | 12/1994 | Shanbrom . |

*Primary Examiner*—Peter F. Kulkosky
*Attorney, Agent, or Firm*—Price, Gess & Ubell

[57] ABSTRACT

An iodine capture system, and related method, comprising a biological liquid conduit and, disposed therein, a polyvinyl acetate-alcohol-acetal porous body, and methods of using the same are disclosed.

2 Claims, 1 Drawing Sheet

TRACE CAPTURE IN BIOLOGICAL FLUIDS

FIELD OF THE INVENTION

This invention relates to the removal of specific trace constituents, principally additives from a previous step, from biological fluids. Such fluids may be liquids or gases. Biological fluids, as the term is used here refers to liquids or gases that are derived from a biological source, contain constituents that originated from a biological source, or that are supplied to a biological system. Without intending any limitation, such fluids would include, by way of example only, blood and blood components, e.g. plasma, serum, clotting factors, etc., suspensions, solutions and emulsions of blood proteins, cells, etc., and nutrients for biological media, such as are used in the propagation of cell lines and air that is provided for breathing by humans, e.g. airline passengers. The invention may also be used with laboratory and other animals. For example, air may be freed of viable pathogens for use by immunodeficient animals to prevent disease. Likewise, air may be pre-treated by means of this invention for use as a carrier for medication to the humans or other animals.

Again without limiting the scope of the field of the invention, the present invention is expected, generally but not always, to be part of a process that includes a step in which one or more materials are added to the fluid to be treated and, after such addition, the fluid is caused to pass through a column, bed, filter, sponge or other solid configuration that acts to remove the residual of the additive, the reaction product or the additive, or some other composition that results because the addition is made. It is known, however, that great care must be taken in preparing particulate filter beds, columns or bodies, to prevent channeling within the bed, column or other body of particles and/or clogging of the filter by fines. Extraordinary care is required to prevent the escape of fines into the effluent treated fluid. The term "fines" is used in its conventional sense as applied to powders, granules, etc., i.e. fines are particles smaller than the size range of the great majority of the particles, e.g. particles of 0.1 to 1 micron that remain in a lot of particles having a nominal size range of 5 to 15 microns. An example, which is in no way limiting, that illustrates the application of the invention is a process in which a biocide is added to a biological fluid to kill bacteria, virus, etc., and thereafter the fluid is passed through a solid configuration as described wherein unreacted biocide, or reaction products of the biocide, or both, are removed by adsorption onto, absorption into or reaction with the solid. In most instances, it is to be expected that some amounts of other constituents of the fluid, e.g. water, etc., may also be removed as an incident to carrying out the process.

In a particularly important application, to which the present application is principally directed, the invention relates to the treatment of human or animal biological liquids, which may contain or carry cells. Liquid and cell-containing liquids from bio-engineering, genetic engineering, etc. are included in the meaning of the term biological liquids as used here.

BACKGROUND OF THE INVENTION

The prior art generally is discussed in some detail in my U.S. Pat. Nos. 5,360,605 and 5,370,869 along with specific discussions of the most relevant prior art references. It is sufficient to summarize the state of the art as follows: After at least three decades of clear recognition of the serious and immediate need for methods to remove pathogenic virus, and other microbes, from blood, blood products, fractions and derivatives, and other biological liquids, the serious and immediate need remains unfilled. After nearly two decades of near panic search for a solution to the aforementioned problem following the catastrophic spreading of AIDS via the blood banking system, the problem remains unsolved in need of an immediate solution on an increasingly urgent basis.

For the three decades referred to, indeed, for almost a century, iodine has been known to all workers to be an effective contact biocide; indeed, iodine, in its various forms, is probably the most widely used and universally known biocidal material in medical history. A history of the relevant uses of iodine and the sources of iodine and iodine compounds is given in my aforesaid United States Patents, the disclosure of which is incorporated herein by reference.

Rubinstein, U.S. Pat. No. 5,185,371, discusses the long standing opposition to the use of iodine in blood which characterized, and still characterizes the general skill of the art. Referring to iodine and other oxidizers, Rubinstein summarizes the prior art in the following terms: "None of these disinfectants have been applied to disinfecting blood products or tissue products. Such compositions in contact with blood and tissue products would cause one to expect resultant damage to the cells and tissue." U.S. Pat. No. 5,185,371, col. 2, lines 43–48. Rubinstein asserts that the well-known disadvantages of iodine as a biocide can be overcome by using iodine in isotonic solutions. Unfortunately, however, even Rubinstein's proposed use of isotonic iodine solutions alone has not solved the long standing and urgent health care problem of infected blood and blood products.

At my direction, a comprehensive survey of the literature on the subject of iodine as a biocide was conducted. Following an analysis of the literature, I concluded, as had most other workers, that there was little hope that iodine or iodine compounds could be used effectively in the processing of blood. Not withstanding the serious problems I set about to develop, if possible, methods for treating blood and blood constituents, plasma in particular, with iodine or iodine compounds to eliminate pathogens, e.g. HIV and hepatitis virus, without altering the biological material to be treated. Many methods have been developed. Much was learned about the use of iodine, in several forms, in biological materials. Several methods that initially appeared attractive, especially considering the overwhelming shadow of doubt that overlies the entire subject, were developed. Very importantly for current products and processes and future research, I have also developed general criteria that relate to the killing of virus in biological fluids, specifically in blood fractions and solutions containing blood constituents. While, it has not always been possible to quantify with exactitude the effect of the various parameters involved certain critical parameters have been discovered and defined.

There is some literature that makes reference to the effect of pH on the virucidal effectiveness of iodine. The problem, however, was defined only in broad terms that were not helpful. Such little definition of the problems as existed were unaccompanied by suggestion as to solving the problems involved in using iodine. It has been established that the virucidal effectiveness of iodine increases as pH decreases below pH 7.0, and, significantly increases as the pH decreases below about 6.0. However, the combination of low pH and iodine alters many blood proteins, certain of the clotting factors in particular, rendering such processes unusable in most situations. This is especially true if iodine is added as Lugol's solution. The addition of comparable amounts of iodine as povidone iodine decreases the rate and/or amount of protein alteration, but also decreases the virucidal effectiveness of iodine on a short contact-time basis. Several approaches were taken to provide iodine-based processes that would reliably and effectively kill pathogenic virus, but no entirely satisfactory iodine-based process has hitherto been found. The term "pathogenic virus" is used here in its ordinarily understood sense to refer to a virus that is capable of causing disease in man or animal.

Many methods and materials exist for introducing iodine into blood fractions and products. Some of these methods and materials show great promise both in providing a high level of virucidal action and in acceptable protein function losses; nevertheless, results are not always consistent and variations in protein function are often great and inexplicable. It has, therefore, become apparent that the use of special methods and materials for introducing iodine into blood and blood products will not, alone, result in a reliable, virucidally effective method for treating such products with acceptable protein function loss.

In general, my work has corroborated the implications of the prior art, namely, that methods based on the use of iodine in blood and blood products are not, alone, satisfactory methods of preparing safe blood products. Iodine could be added by several methods using several iodine source-compounds at such a level as to result in a complete kill of most virus; however, excessive losses of important protein functions, the clotting functions, for example, and degradation of the product occurred. I also explored in considerable depth the use of what I call the "capture" concept, namely the removal of iodine from the blood product after addition of the iodine for biocidal purposes. I determined that there was, in some instances, an advantage in removing the biocidal iodine within a relatively short period of time following addition; however, no entirely satisfactory removal system has heretofore been developed and results were not definitive or consistent. For example, it was known that povidone would "capture" iodine from solution and several forms of povidone were tested as capture materials. Such capture materials were not satisfactory, however, because of incomplete capture and re-iodination from the capture material. Re-iodination occurred when the capture material had absorbed iodine from the liquid being treated. This results in the release of iodine back into subsequent aliquots of such material as it passes through the capture material. Starch is, in theory, an effective capture material, but starch beds or columns tended to channel and/or clog.

The present invention is based on the discovery that a distinctive type of material does not channel or clog and substantially irreversibly captures iodine from biological liquids such as blood, blood fractions and derivatives.

Having experienced years of alternating hope and discouragement and many disappointments in research seeking to use the generally recognized biocidal effectiveness of iodine to treat blood and blood derivatives and products, I have, I believe, discovered one solution to many of the problems predicted by earlier and contemporaneous workers, and which my earlier work established.

SUMMARY OF THE INVENTION

I have discovered materials that are far more effective in removing iodine from blood and blood products, and other biological fluids, and, in some cases, iodide, than materials hitherto known for such applications. Very importantly, I have also found that the use of very high efficiency "capture" materials to remove iodine from such fluids after only a very short contact with iodine or povidone iodine in such biological fluids results in a virucidally effective process without intolerable protein activity destruction.

The materials I have discovered can be made and used in the form of particulate filter or column beds, fibrous beds, columns or bodies, or in any configuration that provides high surface area to contact the fluid to be treated.

A new device for treating liquids that comprise blood, blood fractions or blood derivatives or products is disclosed.

A new method for treating liquids that comprise blood, blood fractions or blood derivatives or products is disclosed.

DESCRIPTION OF THE PREFERRED EMBODIMENTS

Figure 1:
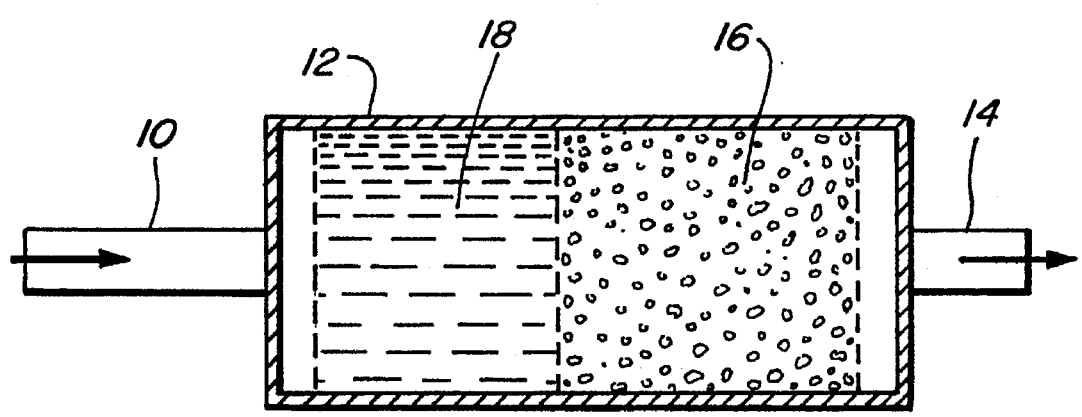
FIG. 1 is a schematic depiction of a device that embodies the invention disclosed herein.

Examples of the invention are provided to illustrate the various forms and applications in which the invention may be used. These are exemplary only and not limiting.

In a very practical embodiment, of the type depicted schematically in FIG. 1, the invention is a device for treating blood, blood plasma, and liquids comprising blood or a blood fraction or component in which blood or a blood fraction or component is a constituent. Typically, such biological liquids are handled in sterile bag systems that permit the liquid to be transferred from one container to another, additives to be incorporated therein, to be divided into components be, for example, expressing plasma through a filter while retaining cells in a container, etc. All this is well-known in the blood banking art. The present device is one component of such a system and may be placed in the system during manufacture, sterilized, stored and handled in the manner currently in practice. The illustrated embodiment of the invention comprises a liquid conduit system and a sponge, the sponge being so configured and constructed in relation to the conduit system as to permit the user to cause the liquid to be treated to pass through the sponge. It will be recognized that an infinite variety of sizes and shapes of the conduit system and sponge, which together comprise the capture system of this invention, are possible.

Referring to FIG. 1, which is schematic only, the capture system comprises a liquid inlet 10, a housing 12, a liquid outlet 14 and a sponge 16. The system may, optionally, also include a bed of particles or other materials as a source of biocidal iodine, though this is not essential to the device as depicted in FIG. 1.

The capture materials of this invention are identified hereinafter generally by the term "polyvinyl acetate-alcohol-acetal porous body." This term, "polyvinyl acetate-alcohol-acetal porous body," is adopted as being as descriptive as any term available but is not a term that has, to the best of my knowledge, a generally accepted meaning in polymer chemistry. By referring to a material as a polyvinyl acetate-alcohol-acetal porous body I mean a material that meets the following criteria. The material will comprise a polymer in which the long chain polymeric structure results substantially from vinyl polymerization and in which substituents along the long chain polymeric structure substantially comprise one or more of the following substituent moieties:

acetate, alcohol or acetal. Of course, the material must not be soluble in water. The body may be integrally formed, e.g. as a single piece sponge, or fabricated, e.g. a fibrous body that is porous, or simply a body constrained by internal or external structures, e.g. a bed of particles or a frit formed of such particles. For example, a frit can be prepared by pressing a body of particles of polyvinyl acetate, polyvinyl acetal or polyvinyl alcohol, of highly uniform size, with or without the addition of heat and/or a poor solvent. The particular nature of the body is retained insofar as surface area for contact is concerned, but the frit is in the desired fixed configuration and is not subject to channeling or clogging with particle fines. The body must, however, be highly porous. Thus far, no great criticality as to pore or passage size has been identified but a pore or passage size in the range of 1 to 1000 microns, typically from 10 to 100 microns, is presently considered to be acceptable for most uses under consideration.

In a more specific sense, particularly in referring to preferred embodiments, the polyvinyl acetate-alcohol-acetal porous body is preferably a biocompatible, polymeric, elastomeric, lint-free, hydrophilic sponge or fibrous body having a generally uniform pore or passage geometry and pore or passage size distribution throughout its volume comprising polyvinyl acetate polymer, polyvinyl acetate-alcohol copolymer or the reaction product of formaldehyde and polyvinyl alcohol. The sponge or fibrous body is characterized by an initial water absorbtion and a wicking point of a maximum of 10 seconds of contact with the body fluid and by a variation in the size of the diameter of the pores of less than about 8 to 1.

While manufacturing methods are not part of this invention, the materials of this invention are typically manufactured by the steps of, first, forming a polymer or copolymer of vinyl acetate, followed by partial hydrolysis of the polymer to the alcohol, or partial or complete hydrolysis followed by acetalization.

Generally, the materials identified as polyvinyl acetate-alcohol-acetal porous bodies will be acceptable for use in contact with biological materials if FDA approved catalysts, etc., are used in the various manufacturing steps.

The preferred capture material is a sponge of the type sold by Merocel Corporation as Merocel® sponge, the characteristics and method of manufacture are described in U.S. Pat. No. 4,098,728 to Rosenblatt, which is a uniformly expandable hydrophilic sponge, adapted for medical usage, characterized by instantaneous wicking and a high liquid holding capacity comprising a reaction product of polyvinyl alcohol and formaldehyde. The wicking and liquid holding capacity is attained by controlling the time, temperature and processing conditions while forming and curing the reaction product in an aqueous medium. The sponge is rendered uniformly expandable by drying the wet sponge while maintaining the shape of the wet sponge. The sponge is biocompatible, non-toxic, lint free, compressible, resilient, strong, non-abrasive, free of foreign leachable materials and is of exceptionally high fluid holding capacity.

Reference is made to U.S. Pat. No. 4,098,728, the disclosure of which is incorporated herein by reference, for further details as to the manufacture of the sponges. In addition, further specifics are available from the manufacturer.

For purposes of identifying such sponges, Rosenblatt's definition is adopted herein, as follows: "A biocompatible, polymeric, elastomeric, lint-free, uniformly swellable hydrophilic sponge having a uniform pore geometry and pore size distribution throughout its volume comprising the inorganic acid-catalyzed reaction product of formaldehyde and polyvinyl alcohol, said sponge being characterized by an initial water absorbtion and a wicking point of a maximum of 10 seconds of contact with the body fluid and by a variation in the size of the diameter of the pores of less than about 8 to 1 as determined by a stereoscopic microscope eyepiece."

The sponge as described has been found to be unique in its avidity for iodine coupled with the near-irreversible nature of iodine uptake from biological solutions. By comparison, povidone is known to have a high avidity for iodine and to have a high iodine loading capacity, but povidone has proven to be less satisfactory as a capture material. Capture, by povidone, is either incomplete or ineffective because, it is believed, povidone binding of iodine is slower than the binding of iodine to the PVAc materials of the present invention, and also because povidone begins to reintroduce iodine into the solution once modest amounts of iodine have been taken up. Contrariwise, Merocel® sponges, when initially free of iodine, take up iodine rapidly and completely. Certainly it would be expected that a highly iodine loaded sponge would constitute a source of iodine—indeed this is known to be the case—the iodine uptake is substantially irreversible until iodine levels in the range of above two or three weight percent are reached. The capture systems of this Invention use such sponges that are initially free of iodine.

This iodine capture material is vastly superior to any previously known capture material. These sponges instantly bind iodine essentially quantitatively, unlike the action of polyvinyl pyrrolidone wherein the iodine uptake is very equilibrium dependent and the binding reaction is comparatively slow. The affinity of the sponges for iodine is far greater than the affinity of polyvinyl pyrrolidone; indeed, these sponge materials readily extract iodine from povidone iodine. The affinity of these sponge materials is comparable to the affinity of starch for iodine, though specific quantitative values have not yet been ascertained. Because the uptake of iodine is fast, instantaneous, and irreversible, and because the sponge does not permit channeling nor contribute fines, it is a very superior capture material—surprising superior as to the iodine uptake characteristics which could not have been and had not been predicted.

Iodine uptake from water is one measure of the sponge's superiority, but such data are not entirely definitive as to biological materials. Iodine in water is present as dissolved iodine, iodide or $I_3^-$, whereas iodine in a biological fluid may be present in these three forms and may be bound, more or less strongly, to any of a large number of cells, proteins, etc. Much remains to be learned about the iodine uptake mechanism from biological fluids but the great superiority of the sponge material has been established.

The invention in this preferred embodiment, then, is embodied in an iodine capture system that comprises a biological liquid conduit and, disposed therein, a biocompatible, polymeric, elastomeric, lint-free, uniformly swellable hydrophilic sponge having a uniform pore geometry and pore size distribution throughout its volume comprising the inorganic acid-catalyzed reaction product of formaldehyde and polyvinyl alcohol, said sponge being characterized by an initial water absorbtion and a wicking point of a maximum of 10 seconds of contact with the body fluid and by a variation in the size of the diameter of the pores of less than about 8 to 1 as determined by a stereoscopic microscope eyepiece.

Other forms of the polyvinyl acetate-alcohol-acetal porous body of this invention may be used. For example, a sponge can be made from polyvinyl acetate or polyvinyl acetate-alcohol copolymer using a froth technique such as described by the Rosenblatt patent referred to above. Polyvinyl acetate sponges will be moderately hydrophilic and rather rigid and brittle, whereas polyvinyl acetate-alcohol sponges will be more hydrophilic, water swellable and more flexible. Likewise fibers can be spun using conventional fiber spinnerettes and the resulting fibers physically formed into a porous body as characterized above. Thin films of polyvinyl acetate or copolymers of polyvinyl acetate-alcohol may be cast as flat or curved films and re-formed, bundled together in proximity to provide flow paths between the grouped films or comminuted and the particles re-formed or confined to form such porous bodies.

Materials that are closely related chemically to the polyvinyl acetate-alcohol-acetal porous bodies of this invention have been used in a variety of biologically related applications. The following uses of related materials, gleaned from literature and patent abstracts, is considered exemplary and illustrative of such uses. Tan, J. H.; et al, (Radiation Research, vol. 124, no. 1, p. 43–9, October 1990) implanted a polyvinyl alcohol sponge disc in the subcutis of the thorax. Criswell, D. W. et al, (Armed Forces Inst. of Pathology, Washington, D.C., Report No.: AFOSR-TR-92-0910) implanted polyvinyl alcohol sponge in mouse subcutaneous tissue to investigate intermittent hyperoxia oxygen treatments and epidermal growth factors. A study of photo-crosslinkable polyvinyl alcohol for bioreactors was reported in Bulletin of Research Institute for Polymers and Textiles, No. 162, 1990-3, Research Inst. for Polymers and Textiles, Yatabe (Japan). Leukocyte filters from polyvinyl alcohol fibers has been reported by Tan, J. H., (Conference Title: Proceedings of the 11th Congress of the International Society for Artificial Cells, Blood Substitutes and Immobilization Biotechnology, (ISABI), Biotechnology 22 5 Nov. 1994, p A64). Sakurada Y., et al, (Polym. J.(Jap.); 19, No. 5, 1987, p. 501–13) describe hollow fibre membranes having blood filtering characteristics and applications to blood purifying devices by spinning polyvinyl alcohol and poly-(alkylene glycol) in water into a coagulation bath of sodium hydroxide/sodium sulphate. Abe Y, et al., (CONFERENCE PROCEEDINGS: Plasmapheresis: New trends in therapeutic applications; Cleveland, Ohio, 25–26 Apr. 1983, p. 295–304. 6S) describes the use of polyvinyl alcohol membranes in plasmapheresis-like applications. A separating agent which includes a polyvinyl acetal resin having open cell structure and an average pore size of from about 10 to about 1000 micrometers has been described by Hiraide Tsuneo et al, (U.S. Pat. No. 5085781). The device also includes porous calcium phosphate granules having open cell structure. Japanese patent no. JP 7025776 describes a filter material made of porous element coated with a polymer having both hydrophobic and polyethylene oxide (PEO) chain parts on the surface and is used for filtration of blood to screen leukocytes. Porous spongy filter elements e.g. polyvinyl alcohol sponges with average fibre sizes of 0.3–3.0 microns and average pore sizes of 2–30 microns are coated with a polymer having hydrophobic part and PEO chain (e.g. methoxytriethylene or hydroxypolyethylene glycol, acrylic acid esters) part. The selective removal of leukocytes to give platelet enriched plasma followed by selective recovery of platelets for blood transfusion or extracorporeal circulation are accomplished. Shevel, E., U.S. Pat. No. 5,370,656 (owened by Merocel Corporation) describes a throat sponge made from polyvinyl acetal that is fast working and expands instantly and uniformly to absorb 23 to 27 times its weight in fluids. The sponge may be pre-hydrated., Polyvinyl alcohol polymers have been studied as a possible support matrix for affinity chromatography in connection with viscous material (e.g., blood plasma), (KANG K; RYU D; DROHAN WN; ORTHNER CL, BIOTECHNOLOGY AND BIOENGINEERING, 1992, V39, N11 (MAY), P1086–1096).

The invention is, in use, embodied in the method of removing iodine from biological liquids comprising passing such liquid(s) through a substantially iodine free biocompatible, polymeric, elastomeric, lint-free, uniformly swellable hydrophilic sponge having a uniform pore geometry and pore size distribution throughout its volume comprising the inorganic acid-catalyzed reaction product of formaldehyde and polyvinyl alcohol, said sponge being characterized by an initial water absorbtion and a wicking point of a maximum of 10 seconds of contact with the body fluid and by a variation in the size of the diameter of the pores of less than about 8 to 1 as determined by a stereoscopic microscope eyepiece. A substantially iodine-free sponge contains less than one percent by weight of iodine.

In another aspect, the invention comprises a method embodying two steps. The first step is the addition of iodine to the biological fluid. The second step is the capture of any residual iodine by the sponge as described. FIG. 1 depicts a source of iodine at 18. This is optional, of course, but in some processes it is advantages to control the contact time of the biological fluid with iodine by positioning the iodine source in the overall liquid handling system and controlling the flow of liquid therein. In the exemplary embodiment of FIG. 1, insoluble povidone iodine (cross-linked povidone—iodine) is provided at 18. The amount and concentration of iodine may, of course, be adjusted as needed sufficient to effect a kill of virus or bacteria, etc., as desired, and, immediately thereafter, preferably within one to five minutes, most preferably under two minutes, passing the iodinated liquid through the capture sponge where the iodine is removed. This technique greatly reduces alteration of proteins and preserves the very labile clotting factors. Over 80% of the available clotting factors can be protected while effecting a complete kill of envelope and non-envelope virus by adjustment of the amount of iodine available and the time of iodine contact with the liquid to be treated.

Biological liquids include, of course, blood, plasma, serum, etc. as well as special solutions containing clotting factors or other blood proteins, cell suspensions and concentrates, and the like.

Pore size of the sponges may be controlled to produce sponges that will effectively separate platelets from liquid blood components. This, in itself, greatly enhances the recovery of valuable blood proteins. On the other hand, large pore size sponges may be used to treat whole blood, platelet-containing liquids, etc.

EXAMPLE 1

Conventional filter funnels were prepared using the polyvinyl acetate-alcohol-acetal porous bodies of this invention. The filter funnel comprises a chamber directly overlaying a filter. The filters were polyvinyl acetal as described above that is commercially available in sheets under the trademark MEROCEL CF 200® and MEROCEL CF 150®. Blood plasma containing EMC virus (encephalomyo-carditis virus) was divided into four aliquots as described below and passed through the polyvinyl acetal filter sponge within one minute±about 30 seconds following mixing. Layers of sponge, one or two layers as indicated below, about ¼ inch thick were used. The amount of two clotting factors, Factor VIII and Factor IX, remaining after the treatment was measured, using the known amount of these factors present before the treatment as the base line. The respective aliquots and the results of this series of tests are given in Table I below, first two entries, along with summary results of a number tests run at different times without capture.

TABLE I

| Aliquot | EMC Kill (Log Kill) | % F VIII (% Remaining) | % F IX |
|---|---|---|---|
| Control | 0 | 100 | 100 |
| 2% (by weight) povidone-Iodine + 2% (by weight Povidone passed through two layers of polyvinyl acetal capture sponge. | Total | 85 | 75 |
| Povidone iodine 0.5 to 5.0 weight percent in plasma, in various tests. | Total | >50 | >50 |

In many of the tests summarized in the third entry, virtually all of the Factor VIII and/or Factor IX activity was lost, and losses of 60% or more were common.

Beds formed of polyvinyl acetate beads take up iodine and experience with hydrolyzed then acetalized polyvinyl acetate provide sound basis for knowing that polyvinyl acetate-alcohol is an equivalent material.

The exact time progression of clotting factor destruction in the presence of iodine is a function of iodine concentration and is believed to be a function of pH and perhaps of temperature and other factors not yet determined. While this time function is not fully understood, it has been established that the contact time of the iodine in blood, plasma, solutions of clotting factors, etc., and other biological solutions comprising labile proteins must be kept to under five minutes and, in most circumstances, must be kept to under two minutes, if labile proteins, clotting factors, etc., are to be preserved.

Capture of the iodine must, of course, be substantially instantaneous and must be certain. Other capture materials have been evaluated. Starch is well-known to react substantially quantitatively with iodine; however, starch beds and even specially prepared starch or amylose beds or columns clog quickly and/or channel and give uncertain results. Povidone is a moderately good capture material but its uptake is slow and it quickly reaches the point where iodine begins to migrate back into the liquid phase. The presence of and generation of fine particles during use is a continuing problem. While this "leaking" of iodine can be overcome to some degree by using deep beds or long columns of insoluble povidone particles, there is nevertheless some continuing iodination of the liquid with resulting loss of functional clotting factors, etc. The polyvinyl acetate-alcohol-acetal porous bodies provide substantially instantaneous quantitative uptake of iodine, no iodine leakage at low levels of iodine uptake, and a free-flowing filter or column construction.

Sponges of the type described are available in a variety of pore sizes and can be made with pores averaging nearly any reasonable size. Such sponges can be used, for example, to treat whole blood wherein all of the blood, including the cells, pass through the sponge. Sponges having a smaller pore size, generally in the range of 2 to 30 microns, e.g. under 10 microns, typically 2–3 microns, may, on the other hand, be used to remove all cellular materials, most particularly platelets, from blood leaving a blood serum-like liquid in which the clotting factors are better preserved than is the case when platelets are present. While Japanese patent no. JP 7025776, according to the abstract thereof, describes a filter material made of porous element coated with a polymer having both hydrophobic and polyethylene oxide (PEO) chain parts on the surface used for filtration of blood to screen leukocytes, no direct use of polyvinyl acetate-alcohol-acetal porous bodies to remove platelets from plasma has been reported. This step can, of course, be carried out while inactivating virus.

Thus, a new and very important result is accomplished by this invention. Contrary to the prior art teachings and my own extensive earlier work, it is now possible to treat blood and blood fractions, products and derivatives with iodine to effect a complete kill of pathogenic virus without loss of the important blood protein functions. Hundreds of millions of dollars have been spent in efforts to provide safe blood and blood constituents without success. This invention makes it possible to achieve the goal that for decades has eluded workers in the blood banking and fractionation industries.

Industrial Application

This invention is useful in the blood banking and blood fractionation industries and in the biotechnology industries generally.

What is claimed is:

1. A method for treating blood, liquid blood fractions or protein solution comprising adding iodine to a biological fluid to be treated and thereafter capturing any residual iodine by passing the iodine-containing biological fluid through a substantially iodine free biocompatible, polymeric, elastomeric, lint-free, uniformly swellable hydrophilic sponge having a uniform pore geometry and pore size distribution throughout its volume comprising the inorganic acid-catalyzed reaction product of formaldehyde and polyvinyl alcohol, said sponge being characterized by a variation in the size of the diameter of the pores of less than about 8 to 1.

2. A method for treating blood, liquid blood fractions or protein solutions, the method comprising the steps of adding iodine to a biological fluid to be treated and thereafter capturing any residual iodine by passing the iodine-containing biological fluid through a substantially iodine free polyvinyl acetate-alcohol-acetal porous body.

* * * * *